United States Patent
Weyer

(10) Patent No.: US 9,737,386 B2
(45) Date of Patent: Aug. 22, 2017

(54) DOSAGE PROJECTILE FOR REMOTELY TREATING AN ANIMAL

(71) Applicant: SmartVet Pty Ltd, Fig Tree Pocket, Queensland (AU)

(72) Inventor: Grant Weyer, Noosa Heads (AU)

(73) Assignee: SmartVet Pty Ltd, Brisbane, Queensland (AU)

( * ) Notice: Subject to any disclaimer, the term of this patent is extended or adjusted under 35 U.S.C. 154(b) by 0 days.

(21) Appl. No.: 14/890,230

(22) PCT Filed: May 8, 2014

(86) PCT No.: PCT/AU2014/000501
§ 371 (c)(1),
(2) Date: Nov. 10, 2015

(87) PCT Pub. No.: WO2014/179831
PCT Pub. Date: Nov. 13, 2014

(65) Prior Publication Data
US 2016/0081782 A1    Mar. 24, 2016

Related U.S. Application Data

(60) Provisional application No. 61/821,789, filed on May 10, 2013.

(51) Int. Cl.
| | | |
|---|---|---|
| *A61K 8/02* | (2006.01) |
| *A61D 7/00* | (2006.01) |
| *A61Q 19/00* | (2006.01) |
| *A61K 8/895* | (2006.01) |
| *A61K 8/06* | (2006.01) |
| *A61K 8/58* | (2006.01) |
| *A61K 8/81* | (2006.01) |
| *F42B 12/40* | (2006.01) |
| *F42B 12/46* | (2006.01) |
| *A61K 9/00* | (2006.01) |
| *A61K 9/48* | (2006.01) |

(52) U.S. Cl.
CPC .............. *A61D 7/00* (2013.01); *A61K 8/0241* (2013.01); *A61K 8/062* (2013.01); *A61K 8/585* (2013.01); *A61K 8/8152* (2013.01); *A61K 8/895* (2013.01); *A61Q 19/00* (2013.01); *F42B 12/40* (2013.01); *F42B 12/46* (2013.01); *A61K 9/0017* (2013.01); *A61K 9/4858* (2013.01); *A61K 2800/412* (2013.01); *A61K 2800/49* (2013.01)

(58) Field of Classification Search
CPC ................ A61K 2800/49; A61K 8/064; A61K 2800/596; A61K 8/0241; A61K 8/895; A61K 2800/412; A61K 8/891; A61K 8/8152; A61K 8/585; A61K 8/062; A61Q 19/00
See application file for complete search history.

(56) References Cited

U.S. PATENT DOCUMENTS

| | | |
|---|---|---|
| 6,524,286 B1 | 2/2003 | Helms et al. |
| 2010/0203122 A1 | 8/2010 | Weyer et al. |

OTHER PUBLICATIONS

International Search Report issued in corresponding International Patent Application No. PCT/AU2014/000501 dated Jun. 11, 2014.

*Primary Examiner* — Carlos Azpuru
(74) *Attorney, Agent, or Firm* — Morgan, Lewis & Bockius LLP

(57) ABSTRACT

The invention relates to a dosage projectile for administering an active agent to an animal, the projectile configured to contain an active agent and having a frangible shell adapted to fragment on impact with an animal to deliver the active agent to the animal and produce a plurality of shell fragments associated with the animal after impact to provide a visible mark on the animal.

15 Claims, No Drawings

DOSAGE PROJECTILE FOR REMOTELY TREATING AN ANIMAL

TECHNICAL FIELD

The invention relates to dosage projectiles for delivering an active agent to an animal. In particular the invention relates to dosage projectiles that shatter on impact with an animal to produce fragments that remain associated with the animal to mark the impact site.

BACKGROUND

The farming of animals, particularly commercially important animals such as cattle typically involves the administration of active agents such as vaccines or pesticides. It is frequently difficult and costly to deliver active agents to animals as this requires herding and containing the animals for that purpose.

A number of prior art treatment systems require delivery of an active agent by piercing the skin or tissue. Although these devices can effectively deliver the desired treatment, often the animal is exposed to the potential of post-treatment infections at the site of delivery. An additional problem with many of the prior art methods is that it can be difficult to determine or monitor which animal has been treated.

Known methods for remotely delivering agents to animals or humans can involve providing of aerosols in close proximity to the animal or person to be treated from a projectile that does not penetrate the skin or tissue. The use of aerosols cannot deliver a defined dosage of an active agent.

WO 2008/0522631 in the name of Smartvet Pty Ltd describes a remote treatment delivery system comprising a dosage projectile containing an active agent and a transdermal carrier. Typically the projectile will split or rupture on contact with an animal and the contents of the projectile, which may include a marker, will be transferred to the animal while the projectile shell falls away. In some cases, depending on the nature of the marker and the colour of the animal it can be difficult to determine which animals have been treated, particularly if the animals are viewed from a distance. In addition, the marker is contained within the projectile and is in solution with the active agent this restricts the choice and amount of marker to those that do not unduly reduce the efficacy of the active agent.

The present inventor has developed a dosage projectile which is configured to fragment on impact with an animal and leave at least some of these fragments of the shell on the skin or fur of the animal to produce a visible mark on the animal at the site of impact.

SUMMARY OF THE INVENTION

In a first aspect the invention provides a dosage projectile for administering an active agent to an animal, the projectile having a frangible shell configured to contain an active agent and adapted to fragment on impact with an animal to deliver the active agent to the animal and produce a plurality of shell fragments associated with the animal after impact to provide a visible mark on the animal.

The visible mark allows determination of which animal in a herd or group of animals has been treated.

In one embodiment the dosage projectile is substantially non-skin piercing.

The frangible shell may be made of plasticized gelatine and sugar alcohol, polystyrene or polystyrene derivatives, hydrophilic colloidal materials, polyolefins such as polypropylene or polyethylene, polycarbonate, polyamide, polyvinylchloride, resinous compounds, thermoplastic polyesters such as polylactic acid, thermoplastic starch polymer blends, or combinations thereof.

It is contemplated that any known plasticized gelatine and sugar alcohol may be suitable for manufacturing the dosage projectile. The sugar alcohol may be from glycol, glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol, polyglycitol or combinations thereof.

In one embodiment the frangible shell is biodegradable.

For capsule shells composed of plasticized gelatin, the anhydrous shell composition may include from about 20% to 70% of a polyol or polyol blend, including but not limited to, glycerol, maltitol, xylitol, sorbitol, sorbitan, propylene glycol, polyethylene glycol, and mannitol. The gelatin polymer composition may contain from 1% to 5% additives including colorants, opacifiers, lubricants, and antifoam agents.

The frangible shell may contain or be coated with a marker. The marker may be selected from a water insoluble dye, water soluble dye, pigment, Lake dye, infra-red dye, ultraviolet dye, a luminescent dye, coloured paint, reflective, refractive, fluorescent or luminescent material.

In some embodiments the shell fragments may be refractive, reflective, coloured, fluorescent, or luminescent.

In one embodiment the shell fragments mark the animal for a period of time to allow confirmation that an animal has been treated. For example, a period of about 20 minutes to 3 hours may be suitable. In some embodiments marking is for up to about 72 hours can be desirable.

The dosage projectile is capable of being remotely delivered over a distance.

The active agent may be a pharmaceutical, veterinary pharmaceutical, vaccine or immunogenic compound, parasiticide, pesticide, or health supplement.

In some embodiments the pharmaceutical or veterinary pharmaceutical can be macrocyclic lactones, synthetic pyrethroids, insect growth regulators, anthelminitics, steroid hormones, anaesthetic agents and analgesics, antibacterial or antibiotic agents, anthelmintic, anti-trematodal, anticestodal, anti-parasitic/parasiticidal agents, acaricidal agents, anti-fungal agents, antihistamine agents, antiviral agents, anxiolytic agents, β-adrenergic agonists, bronchodilators, anti-allergy agents, cardioactive agents, central nervous system stimulants and agents, cholinergic agents, anti-cholinergic agents, anti-emetic agents, or muscle relaxants.

In some embodiments the health supplement can be a vitamin or mineral.

In some embodiments the pharmaceutical or veterinary pharmaceutical may be a macrocyclic lactone such as ivermectin, eprinomectin, moxidectin, selamectin, doramectin, milbemycin, abamectin, cydectin and emamectin benzoate.

In some embodiments the pesticide is a synthetic pyrethroid such as lambda cyhalothrin, flumethrin, deltamethrin, cypermethrin, cyfluthrin, fenvalerate, alphacypermethrin and pyrethrin.

In some embodiments the pesticide is an insect growth regulator such as pyriproxifen, methoprene, cyromazine, lufenuron, diflubenzuron, fluazuron, dicyclanil and fluazuron.

In some embodiments the pesticide is an antihelminthic such as, imidacloprid, rotenone, magnesium flurosilicate, piperonyl butoxide, spinosyns and benzimidazoles such as albendazole, oxfenbendazole, fenbendazole.

In one embodiment the pesticide may be an immunomodulator, for example levamisole.

In one embodiment the pesticide may be a pro-insecticide being a compound that is metabolized into an active insecticide after entering the host or target insect. The pro-insecticide may be derived from a microbially produced compounds for example halogenated pyrroles, an example of this class being chlorfenapyr.

In one embodiment the pesticide may be encapsulated or micro-encapsulated in one or more encapsulating or coating agents in order to more effectively control the delivery of the pesticide to the animal. The encapsulating or coating agent may be chosen such that it regulates the release of the pesticide once it has been deposited onto the skin or absorbed into the blood stream or lymphatic system of the animal.

In some embodiments the active agent is a vaccine or immunogenic compound. In embodiments where the active agent is a vaccine or immunogenic compound the dosage projectile may further include one or more adjuvants.

The vaccine my be a vaccine for Foot and Mouth, Bovine Tuberculosis, Tuberculosis, or other live, dead, attenuated or other vaccine known to the art to expose a treated animal to pathogenic organisms in a manner that provokes an immune response.

In some embodiments the health supplement may be a vitamin or mineral, for example calcium, potassium, iron, thiamine and Vitamin B12.

In some embodiments that active agent is a contraceptive.

The active agent may be present in any suitable solvent or liquid, such as, isopropyl alcohol; dipropylene glycol methyl-ether; butylated hydroxytoluene dipropylene glycol monomethyl-ether; methylene chloride; diethyl ether, ethanol, acetonitrile, ethyl acetate, benzyl alcohol and a combination of natural oils.

In another embodiment the dosage projectile further includes a transdermal carrier. The transdermal carrier may be selected from isopropyl alcohol; dipropylene glycol methyl-ether; butylated hydroxytoluene dipropylene glycol monomethyl-ether; methylene chloride; diethyl ether, ethanol, acetonitrile, ethyl acetate, benzyl alcohol and a combination of natural oils. ethylene glycol, propylene glycol, dimethyl polysilaxane (DMPX), oleic acid, caprylic acid, 1-octanol, ethanol (denatured or anhydrous), liposomal compositions, suitable plant oils, such as Aloe vera derivatives or sesame seed oil or derivatives thereof, acrylic polymers, rubber-based polymers, polysilcxane-based polymers, polyvinylpyrrolidone-based polymers, dimethylsulfoxide (DMSO), dimethylformamide (DMF), lecithin, bi-component aggregates such as Transfersomes®, ethosomes, ozone, castor oil derivatives, such as ethoxylated castor oil, jojoba oil derivatives, corn oil derivatives, emu oil derivatives or mixtures thereof.

In a second aspect the invention provides a method of remotely treating an animal comprising:

launching a dosage projectile cording to the first aspect of the present invention at an animal;

impacting the projectile on the animal causing the frangible shell of the projectile to shatter and release of the active agent on the skin, coat or fur of the animal, and producing a plurality of shell fragments associated with the animal after impact to provide a visible mark on the animal.

In one embodiment there is no substantial piercing of the skin of the animal by the projectile.

In a third aspect there is provided a use of a dosage projectile according to the first aspect in a method of treating an animal.

The animal may be ovine, bovine, equine, leporine, porcine, feline, canine, caprine or avian. Preferably, the animal is bovine.

The dosage projectile can be formulated to treat target pests such as horn fly, face fly, stable fly, heel fly, warble fly, bat fly, house fly, horse fly, deer fly, blow fly, mosquito, midge, louse, tick, and mite. The target pest may be a helminth such as a roundworm, stomach worm, tapeworm, or fluke. The target pest may be a protozoan such as a coccidian. In some embodiments the target pest may be a larvae, pupae or egg.

The dosage projectile can be formulated for vaccine delivery, providing health supplements, and the like.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form component of the prior art base or were common general knowledge in the field relevant to the present invention as it existed in Australia prior to development of the present invention.

This application claims priority to U.S. provisional patent application No. 61/821,789 filed 10 May 2013 which is herein incorporated by reference in its entirety.

In order that the present invention may be more clearly understood, preferred embodiments will be described with reference to the following drawings and examples.

Definitions

The term 'active agent' is intended to have the broadest meaning and includes at least one of any therapeutic, prophylactic, vaccine, antigenic, pharmacological, anti infective (antibiotic or antiseptic) or physiologically active substance, which is deliverable to an animal to produce a desired, usually beneficial, effect. More specifically, the term 'active agent' is used herein to refer to any active agent that is capable of producing a pharmacological response, localized or systemic, irrespective of whether therapeutic, diagnostic, or prophylactic in nature. It should be noted that the active agents can be used singularly or in combinations and mixtures as required.

As used herein, the term 'pest' refers to any organism or microorganism that negatively affects an animal by colonisation, infection or transient, periodic or continual association with the animal. The term 'pest' includes organisms that spread disease and/or compete with an animal for nutrients. In addition, a pest is any organism or microorganism known to associate with an animal and which, as a result of that association, causes a detrimental effect on the animal's health and vigour. The term 'pest' refers to an individual pest organism or microorganism or a population of pest organisms or microorganisms.

As used herein, the term 'pesticide' refers to any substance that can be used in the control of a pest, that is, a pesticide is any substance that can prevent association of a pest with an animal, destroy or repel a pest, or mitigate the effect of a pest on an animal. The term 'pesticide' also refers to naturally occurring and synthetic chemicals and chemicals synthetically derived from naturally occurring compounds.

As used herein the term 'remote delivery' refers to any method of delivering a pesticide to an animal which does not require immediate proximity to the animal.

Unless the context requires otherwise or specifically stated to the contrary, integers, steps, or elements of the invention recited herein as singular integers, steps or elements clearly encompass both singular and plural forms of the recited integers, steps or elements.

The term 'animal' is to be accorded its widest meaning, and includes humans and individuals of any species of social, economic or research importance including but not limited to members of the genus ovine, bovine, equine, porcine, feline, canine, primates (including human and non-human primates), rodents, murine, caprine, leporine, and avian. In preferred embodiments the animal is a bovine animal.

Those skilled in the art will appreciate that the invention described herein is susceptible to variations and modifications other than those specifically described. It is to be understood that the invention includes all such variations and modifications. The invention also includes all of the steps, features, compositions and compounds Throughout this specification, unless the context requires otherwise, the word 'comprise', or variations such as 'comprises' or 'comprising', will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

As used herein, the singular form 'a', 'an' and 'the' include plural references unless the context clearly dictates otherwise.

DETAILED DESCRIPTION

The present invention provides dosage projectiles that shatter on impact with an animal to produce fragments that remain associated with the animal to mark the impact site. The invention also provides methods of using the dosage projectiles for treating animal.

Dosage Projectiles

Typically the dosage projectiles of the invention are made from a substance such as, but not limited to, hydrophilic colloidal materials such as, gelatin, albumin, gum arabic, alginate, casein, agar or pectins, or combinations thereof. The projectile can also be made from a synthetic organic compound such as, but not limited to, polystyrene, polypropylene, polyethylene, polycarbonate, polyamide, polyvinylchloride, resinous compounds such as fibreglass or Perspex derivatives, thermoplastic polyesters such as polylactic acid, thermoplastic starch polymer blends, or combinations thereof.

It is contemplated that any known plasticized gelatine and sugar alcohol may be suitable. The sugar alcohol may be selected from the group consisting of glycol, glycerol, erythritol, threitol, arabitol, xylitol, ribitol, mannital, sorbitol, galactitol, fucitol, iditol, inositol, volemitol, isomalt, maltitol, lactital, rnaltotriitol, maltotetraitol, and polyglycitol.

An example of a suitable anhydrous gelatin capsule shell composition is shown in the Table 1 below.

TABLE 1

| N | Ingredient | Amount (mg) |
|---|---|---|
| 1 | Gelatine Bovine Skin | 536.4 |
| 2 | Glycerol | 63.1-242.5 |
| 3 | Maltitol | 81.2-161.0 |
| 4 | Sorbitol | 80.5-98.2 |
| 5 | Mica | 4.2 |
| 6 | Titanium dioxide | 7.0 |
| 7 | FD&C 6 Sunset yellow | 9.9 |
| | Total approx. | 800.00 |

For capsule shells composed of plasticized gelatin, the anhydrous shell composition may comprise from about 20% to 70% of a polyol or polyol blend, including but not limited to glycerol, maltitol, xylitol, sorbitol, sorbitan, propylene glycol, polyethylene glycol, and mannitol. For capsule shells composed of plasticized gelatin, the anhydrous shell composition may comprise from about 20% or 25% or 30% or 35% or 40% or 45% or 50% or 55% or 60% or 65% or 70% of a polyol or polyol blend, including but not limited to, glycerol, maltitol, xylitol, sorbitol, sorbitan, propylene glycol, polyethylene glycol, and mannitol.

The gelatin polymer composition may contain from about 1% to 5% additives including colorants, opacifiers, lubricants, and antifoam agents. The gelatin polymer composition may contain from about 1% or 2% or 3% or 4% or 5% additives including colorants, opacifiers, lubricants, and antifoam agents.

Inclusion of the sugar alcohol and a gelatine polymer in the projectile shell preferably results in a frangible shell that is adapted to shatter on impact with the animal to produce a plurality of shell fragments that leave a mark on the skin, fur or coat of an animal.

The mark formed by the projectile on the animal is typically temporary. The mark can remain on the animal for a period of a few minutes to about 72 hours. The mark can remain on the animal for a period of a few minutes, a few hours, 6 hours, 12 hours, 18 hours, 24 hours, 30 hours, 36 hours, 42 hours, 48 hours, 54 hours, 60 hours, 66 hours or 72 hours.

In order to enhance the visibility of the mark the frangible shell may contain or be coated with a marker material. The marker may be a pharmaceutically acceptable dye, coloured paint, fluorescent, reflective, refractive or luminescent material. The dye or marker may be brightly coloured to allow a person administering the treatment to see readily which animals have been treated.

The marker may be a pharmaceutical, food, or cosmetic colorant, oil based paint or colorant, pigment, or dye. Examples of suitable marking components include liquid dyes, powder dyes, water soluble dyes, infra-red dyes, ultraviolet dyes, or dyes that glow in the dark (eg chemiluminescent dyes or phosphorescent dyes).

The marker may be fluorescent or luminescent, rendering animals which have been marked or treated under low-light conditions easily visible. The marker andfor solution may also contain a radioactive or other suitable tracking component.

The marker may be present as a coating on at least part of the projectile, as part of the projectile shell or as a component of the composition part of the contents of the projectile. For example, the projectile may be painted with a coloured paint or dye. In other embodiments the composition used to make the projectile shell may include for example a dye or luminescent, fluorescent, refractive or reflective material.

Active Agents

The dosage projectiles of the invention include a biologically active agent. The active agent can be formulated for topical use or systemic use. The active agent can be encapsulated in a controlled-release coating prior to inclusion in the projectile thereby allowing the controlled release of the active agent on or in an animal to be treated. The controlled-release coating may be selected from controlled release compositions known in the field.

The dosage projectiles of the invention typically include an active agent, and optionally a transdermal carrier. The active agent can be encapsulated in a controlled-release coating prior to inclusion in the projectile thereby allowing the controlled release of the active agent within an animal to be treated, once it has passed transdermally into the blood or lymphatic system of the animal. The controlled-release coating may be selected from controlled release compositions known in the field.

Although it is within the contemplation of the invention that externally administrable active agents may also be included within the projectile, the invention is especially suited to delivering systemic treatments for the treatment of endoparasites or ectoparasites to animals. The active agents may be absorbed by and distributed through the blood or lymphatic system of an animal once it has been absorbed though the skin of an animal. Thus the active agents are deliverable to animals by absorption through the skin, and not necessarily by a piercing element or needle, so that animals may be treated systemically, substantially without insulting the skin of the animal.

It is to be appreciated that the viscosity of the projectile contents should be such that the contents do not run off the skin, fur or coat of the animal prematurely before treatment has occurred. Accordingly, the projectile may also include a thickening agent, such as a starch-like compound, inert polymer, gel, or an oil-based composition such as sesame seed oil, if required.

The active agent or agents contained in the projectile can be in different forms and/or concentrations, depending on the formulation, the carrying capacity, and solubility and release characteristics desired, for example as neutral molecules, components of molecular complexes, and pharmaceutically acceptable salts, free acids or bases, or quaternary salts thereof. Simple derivatives of the active agents mentioned herein, such as pharmaceutically acceptable ethers, esters, amides and the like which have desirable retention and release characteristics in vivo, and enzymes, pro-active forms, pro-drugs and the like, can also be employed as required.

The amount of active agent to be complexes with the transdermal carrier will vary depending on the particular active agent, the desired therapeutic effect, and the time span for which the active agent is to be therapeutically effective. Normally, the amount of active agent in the transversal system can vary from about 0.1% to about 50% or even from about 0.1% to about 30% by weight based on the dry weight of the total carrier composition. Persons skilled in the art will be able to determine the adequate amounts required for each application, as required. For examples, for lower dose concentrations, such as with steroidal hormones or corticosteroids, the preferred amount need only be for example from about 01% to about 10%.

In some embodiments the active agent is an anti-infective or health supplement such as a mineral or vitamin, other active agents or specific pesticide drug which may be employed more specifically in embodiments of the invention include, but are not limited to: Macrocyclic Lactones including the avermectins and milbemycins, for example Ivermectin, eprinomectin, moxidectin, selamectin, doramectin, milbemycin, abamectin, cydectin and emamectin benzoate.

Synthetic pyrethroids such as cyhalothrin, lambda cyhalothrin, gamma cyhalothrin, fiumethrin, deltamethrin, cypermethrin, cyfluthrin, fenvalerate, alphacypermethrin and pyrethrin.

Insect Growth Regulators such as yriproxifen, methoprene, cyro azine, lufenuron, diflubenzuron, fluazuron, dicyclanil and fluazuron.

Other anthelminitics and related compounds such as fipronil, imidacloprid, rotenone, Mg flurosilicate, piperonyl butoxide, spinosyns and other suitable benzimidazole anthelmintics and immunomodulators (e.g. Levamisole).

In one embodiment, the active agent is a transdermal immunization composition, including *Vibrio cholera* toxin, tetanus toxoid, bacterial ADP ribosylating exotoxin (bARE), Foot and Mouth Disease antigens, tuberculosis antigens, and/or *Escherichia coli* heat-labile enterotoxin, and/or mutants and derivatives thereof. It also includes a mixture of any such transdermal immunization compositions and/or other medicaments. The transdermal immunization compositions or mixtures thereof may be made up in any suitable solvent or liquid, such as, but not limited to, water or alcohol. The transdermal immunization compositions can further serve as transdermal carriers in their own right, in that they facilitate the dermal penetration of other active agents, compositions, polypeptides, oligopeptides, or peptide fragments.

The active agents can include steroid hormones such as estrogens, for example colpormon, conjugated estrogens, estradiol and estradiol esters (e.g. acetate, benzoate, cypionate, dipropionate diacetate, enanthate, undecylate and valerate), estriol, estrone, ethinyl estradiol, equilenin, equilin, mestranol, moxestrol, mytatrienedial, quinestradiol and quinestrol; progestagenically effective steroid hormones such as allylestrenol, anagestone, chlormadinone acetate, delmadinone acetate, demegestone, desogestrel, 3-keto desogestrel, dimethisterone, dydrogesterone, ethinylestrenol, ethisterone, ethynodiol (and diacetate), flurogestone acetate, gestodene, gestonorone caproate, haloprogesterone, (17-hydroxy- and 17-acetate-) 16-methylene-progesterone, 17α-hydroxyprogesterone (acetate and caproate), levonorgestrel, lynestrenol, medrogestone, medroxyprogesterone (and acetate), megestrol acetate, melengestrol, norethindrone (acetate and enanthate), norethisterone, norethynodrel, norgesterane, norgestimate, norgestrel, norgestrienone, 19-nonprogesterone, norvinisterone, pentagestrone, progesterone, promegestone, quingestrone and trengestone; androgenically effective steroid hormones such as aldosterone, androsterone, boldenone, cloxotestosterone, dehydroepiandrosterone, fluoxymesterone, mestanolone, mesterolone, methandrostenolone, methyltestosterone, 17α-methyltestosterone, 17α-methyltestosterone 3-cyclopentyl enol ether, norethandrolone, normethandrone, oxandrolone, oxymesterone, oxymetholone, prasterone, stanlolone, stanozolol, testosterone (acetate, enanthate, isobutyrate, propionate and undecanoate), testosterone-17-chloral hemi-acetal, testosterone-17β-cypionate, or tiomesterone.

Other active agents or specific drugs which may be employed in embodiments of the invention include, but are not limited to:

Anaesthetic agents and analgesics, such as benzocaine, bupivicaine, capsaicin, cocaine, dibucaine, dyclonine, etidocaine, lidocaine, mepivacaine, prilocaine, procaine and tetracaine, acetaminophen, acetylsalicylic acid, buprenorphine, codeine, fentanyl, hydromorphone lisuride, salicylic acid derivatives, sufentanil and sumatriptan.

Antibacterial or antibiotic agents such as aminoglycosides, β-lactams, cephamycins, macrolides, penicillins, polypeptides and tetracyclines.

Anthelmintic, anti-trematodal, anticestodal, or anti-parasitic/parasiticidal agents such as albendazole, levamisole, mebendazole, pyrantel, praziquantel, moxidectin, ivermectin, oxamniquine, metrifonate, piperazine, thiabendazole, tiabendazole, diethylcarbamazine, pyrantel, niclosamide, doramectin, eprinomectin, morantel, oxfendazole, dichlorvos, chlorsulon and selamectin.

Acaricidal agents including antibiotic acaricides, nikkomycins, thuringiensin, macrocyclic lactones, acaricides, tetranactin, bridged diphenyl acaricides, azobenzene, benzoximate, benzyl benzoate, bromopropylate, chlorbenside, chlorfenethol, chlorfenson, chlorfensulphide, chlorobenzilate, chloropropylate, cyflumetofen, dicofol, diphenyl sulfone, dofenapyn, fensan, fentrifanil, fluorbenside, proclonol, tetradifon, tetrasul, carbamate acaricides, benomyl, carbanolate, carbaryl, carbofuran, methiocarb, metolcarb, promacyl, propoxur, oxime carbamate caricides, aldicarb, butocarboxim, oxamyl, thiocarboxime, thiofanox, dinitrophenol acaricides, binapacryl, dinex, dinobuton, dinocap, dinocap-6, dinocton, dinopenton, dinosulfon, dinoterbon, DNOC, formamidine acaricides, amidines, amitraz, chlordimeform, chloromebuform, formetanate, formparanate, mite growth regulators, clofentezine, diflovidazin, dofenapyn, fluazuron, flubenzimine, flucycloxuron, flufenoxuron, hexythiazox, arganochlorine acaricides, bromocyclen, camphechlor, dienochlor, endosulfan, lindane, organophosphorus acaricides, organophosphate acaricides, chlorfenvinphos, crotoxyphos, dichlorvos, heptenophos, mevinphos, monocrotophos, TEPP, tetrachlorvinphos, organothiophosphate acaricides, amidithian, amiton, azinphos-ethyl, azinphos-methyl, azothoate, benoxafos, bromophos, bromophos-ethyl, carbophenothion, chlorpyrifos, chlorthiophos, coumaphos, cyanthoate, demeton, demeton-O, demeton-S, demeton-methyl, demeton-O-methyl, demeton-S-methyl, demeton-S-methylsulphon, dialifos, diazinon, dimethoate, dioxathion, disulfoton, endothion, ethion, ethoate-methyl, formothion, malathion, mecarbam, methacrifos, omethoate, oxydeprofos, oxydisulfoton, parathion, phenkapton, phorate, phosalone, phosmet, phoxim, pirimiphos methyl, prothidathion, prothoate, pyrimitate, quinalphos, quintiofos, sophamide, sulfotep, thiometon, triazophos, trifenofos, vamidothion, phosphonate acaricides, trichlorfon, phosphoramidothioate acaricides, isocarbophos, methamidophos, propetarnphos, phosphorodiamide caricides, dimefox, mipafox, schradan, organotin acaricides, azocyclotin, cyhexatin, fenbutatin, phenylsulfamide acaricides, dichlofluanid, phthalimide acaricides, dialifos, phosmet, pyrazole acaricides, acetoprole, fipronii tebufenpyrad, vaniliprole, pyrethroid acaricides, pyrethroid ester caricides, acrinathrin, bifenthrin, cyhalothrin, cypermethrin, alpha-ypermethrin, fenpropathrin, fenvalerate, flucythrinate, flumethrin, fluvalinate, tau-fluvalinate, permethrin, pyrethroid ether acaricides, halfenprox, pyrimidinamine acaricides, pyrimidifen, pyrrole acaricides, chlorfenapyr, guinoxaline acaricides, chinomethionat, thioquinox, sulfite ester caricides, propargite, tetrazine acaricides, clofentezine, diflovidazin, tetronic acid acaricides, spirodiclofen, thiocarbamate acaricides, fenothiocarb, thiourea acaricides, chloromethiuron, diafenthiuron, unclassified acaricides, acequinocyl, amidoflumet, arsenous oxide, bifenazate, closantel, crotamiton, disulfiram, etoxazole, fenazaflor, fenazaquin, fenpyroximate, fluacrypyrim, fluenetil, mesulfen, MNAF, nifluridide, pyridaben, sulfiram, sulfluramid, sulfur triarathene.

Anti-fungal agents such as clortrimazole, ketoconazole, miconazole, nystatin and triacetin.

Antihistamine agents such as tricyclics such as ahistan, etymemazine, fenethazine, n-hydroxyethylpromethazine chloride, isopromethazine, mequitazine, promethazine, pyrathiazine, and thiazinamium methyl.

Anti-inflammatory and/or corticoid agents such as beclomethasone, betamethasone (and acetate, diprorionate and valerate), corticosterone, cortisone, deoxycortocosterone (and acetate), dexamethasone, diclofenac, fenoprofen, flucinolone (and acetonide), fludrocortisone, fluocinonide, flunisolide, fluradrenolide, flurbiprofen, halcinonide, hydrocortisone (and acetate), ibuprofen, ibuproxam, indoprofen, ketoprofen, ketorolac, naproxen, oxametacine, oxyphenbutazone, piroxicam, prednisolone, prednisone, suprofen and triamcinolone (and acetonide).

Antiviral agents such as acyclovir, rimantadine and vidarabine.

Anxiolytic agents such as azapirones such as buspirone and ipsapirone, benzodiazepines such as alprazolam, chlordiazepoxide, clonazepam, clorazepate, diazepam, flurazepam, halazepam, lorazepam, oxazepam, oxazolam, prazepam and triazolam.

β-Adrenergic agonist agents such as albuterol, carbuterol, fenoterol, metaproterenol, mirtazapine, rimiterol, quinterenol, salmefamol, soterenol, tratoquinol, terbutaline and terbuterol.

Bronchodilators such as ephedrine derivatives including:

Anti-allergy agents such as amlexanox, astemizole, azelastine, cromolyn, fenpiprane, ibudilast, nedocromil, oxatomide, pentigetide, repirinast, tranilast and traxanox.

Cardioactive agents such as atenolol, benzydroflumethiazide, bendroflumethiazide, calcitonin, captopril, chlorothiazide, clonidine, clopamide, dobutamine, dopamine, diltiazem, enalapril, enalaprilat, gallopamil, indomethacin, isosorbide (dinitrate and mononitrate), monoxidil, nicardipine, nifedipine, nitroglycerin, papaverine, prazosin, procainamide, propranolol, prostaglandin $E_1$ and $E_2$, quinidine.

Central Nervous System stimulants and agents such as dextroamphetamine, methylphenidate, and nicotine.

Cholinergic agents such as acetylcholine, arecoline, bethanechol, carbachol, choline, methacoline, muscarine and pilocarpine.

Anti-cholinergic agents such as atropine, eucatropine and procyclidine.

Anti-emetic agents such as acetylleucine monoethanolamine, alizapride, benzquinamide, bietanautine, bromopride, buclizine, chlorpromazine, clebopride, cyclizine, dimenhydrinate, dipheniodol, domperidone, granisetron, meclizine, methalltal, metoclopramide, metopimazine, nabilone, ondansteron, oxypendyl, pipamazine, piprinhydrinate, prochlorperazine, scopolamine, tetrahydrocannabinols, thiethylperazine, thioproperzaine, trimethobenzamide and tropisetron.

Muscle relaxants such as Baclofen.

The projectiles may have sufficient volume to contain a unit dosage for a certain disease for an animal. The dosage is typically calculated to correspond to a certain minimum weight of animal to which an active agent is to be administered. If larger animals need to be treated, the number of projectiles launched at the animal may be increased accordingly.

For example, in order to treat an animal weighing, for example, 150 kg, a single projectile containing a unit dosage may be enough. However, in order to provide a sufficiently efficacious dose to a larger animal such as a steer weighing, for example 300 kg, two projectiles may be required.

The amounts of the active agent used in a projectile may be determined by methods known to persons skilled in the field of the invention. Amounts typically range from about 0.05 mg to about 20,000 mg and preferably from about 0.1 mg to about 1,000 mg, depending on the active agent, the disease to be treated, the animal species, and the size of the animal. In certain embodiments of the invention, the active agents may be included in a range from about 0.1 to about 500 mg per mammal per 50 kg body weight.

In embodiments where a transdermal carrier is used, the transdermal carrier is typically used in an amount of about 5% to about 95%, and preferably from about 10% to about 75%, by weight based on the dry weight of the total carrier composition.

The transdermal carrier composition of the present invention can also contain one or more solvents and/or co-solvents known in the art.

Suitable solvents and co-solvents include volatile substances or compositions such as alcohols, aromatic hydrocarbons such as benzene derivatives, lower molecular weight alkanes and cycloalkanes, alkanoic acid esters, polyhydric alcohols, which include glycols, triols and polyols such as ethylene glycol, diethylene glycol, propylene glycol, dipropylene glycol, trimethylene glycol, butylene glycol, polyethylene glycol, hexylene glycol, polyoxethylene, glycerin, trimethylpropane, sorbitol, polyvinylpyrrolidone, glycol ethers such as ethylene glycol monoethyl ether, glycol esters, glycol ether esters such as, ethylene glycol monoethyl ether acetate and ethylene glycol diacetate; saturated and unsaturated fatty acids, mineral oil, silicone fluid, lecithin, retinol derivatives and the like, water, and ethers, esters and alcohols of fatty acids or combinations and mixtures thereof.

Although the exact amount of solvents and co-solvents that may be used in the carrier composition depends on the nature and amount of the other ingredients, such amount typically ranges from about 0.1% to about 40%, and preferably from about 0.1% to about 30% by weight, and mare preferably from about 1% to about 20%, by weight based on the dry weight of the total carrier composition.

The transdermal carrier is typically selected so that it may be readily absorbable by the skin of an animal without causing undue itching, irritation, or toxic effects to the animal. Selection of the transdermal carrier will also depend on the active agent to be delivered to an animal and also the type of animal to be treated, or the intended delivery site on an animal. Thus, the transdermal carrier composition 16 may be selected to suit the charge, size, hydrophobicity, hydrophilicity, amphipathicity, pI, pH, decay rate, or other relevant criteria of the active agent to be carried transdermally, while also being readily absorbable through the skin of an animal.

In one preferred form, the dosage projectile further includes a transdermal carrier as defined in WO 20081052263 assigned to SmartVet Pty Ltd. In this form, the pesticide may be transported (with the aid of a transdermal agent) through the skin following rupturing of the projectile upon contact with the animal, penetration of the pesticide being effected by the transdermal carrier contained within the projectile. In use the transdermal carrier facilitates passage of the pesticide through the skin of an animal in need of treatment.

It is to be understood that any suitable transdermal carrier or solvent which facilitates transdermal absorption of the pesticide may be used. Typically, the transdermal carrier includes carriers such as isopropyl alcohol, dipropylene glycol methyl-ether, butylated hydroxytoluene dipropylene glycol monomethyl-ether, 1-methoxy 2-propanol (glysolv PM/icinol PM), Ethylene glycol monobutylether (butyl glyxolv/butyl icinol), Butyl di glysolv (butyl-icinol), Transcutol, propylene glycol (PG), N-methyl-2 pyrrolidone (NMP), methylene chloride, diethyl ether, ethanol, acetonitrile, ethyl acetate, benzyl alcohol and a combination of natural oils; ethylene glycol, propylene glycol, dimethyl polysiloxane (DMPX), oleic acid, caprylic acid, 1-octanol, ethanol (denatured or anhydrous), liposomal compositions, suitable plant oils, such as Aloe vera derivatives or sesame seed oil or derivatives thereof, acrylic polymers, rubber-based polymers, polysiloxane-based polymers, polyvinylpyrrolidone-based polymers, dimethylsulfoxide (DMSO), dimethylformamide (DMF), lecithin, [g1]Any artificial vesicles which are designed to mimic a cell vesicle and deliver drugs or genetic material into a cell. The bounding membrane of which may be more flexible than that of a standard liposome, allowing it to deform and pass through openings in a barrier, such as the skin, whose diameters are much smaller than the average vesicle size. A Transfersome® is a bi-component, most often vesicular, aggregate. The main functional characteristic of the aggregate is the extreme flexibility and permeability of its bilayer-like membrane coating. The basis of this characteristic is the interdependency of local membrane shape and composition, which makes the bilayer self-regulating and self-optimising. The bilayer is thus capable of stress adaptation, via local and reversible bilayer component demixing. These characteristics make Transfersomes® a device suitable for non-invasive and targeted drug delivery, including across intact skin.

Additional transdermal carriers include, but are not limited to, ethosomes, atone, castor oil derivatives, such as ethoxylated castor oil, jojoba oil derivatives, corn oil derivatives, emu oil derivatives, or any other suitable transdermal or transcutaneous carrier or carrier composition.

Preferably, the transdermal carrier is propylene glycol, DMSO, alcohol or a more penetrant adjuvant known to the art.

In certain embodiments of the invention, an enhancer is incorporated into the carrier composition. An 'enhancer' as used herein refers to substances used to increase permeability and/or accelerate the delivery of an active agent through the skin of an animal, and include monohydric alcohols such as ethyl, isopropyl, butyl and benzyl alcohols; or dihydric alcohols such as ethylene glycol, diethylene glycol, or propylene glycol dipropylene glycol and trimethylene glycol; or polyhydric alcohols such as glycerin, sorbitol and polyethylene glycol, which enhance drug solubility; polyethylene glycol ethers of aliphatic alcohols (such as cetyl, lauryl, oleyl and steady) including polyoxyethylene-4-lauryl ether, polyoxyethylene-2-oleyl ether and polyoxyethylene-10-oleyl ether; vegetable, animal and fish fats and oils such as cotton seed, corn, safflower, olive and castor oils, squalene, and lanolin; fatty acid esters such as propyl oleate, decyl oleate, isopropyl palmitate, glycol palmitate, glycol laurate, dodecyl myristate, isopropyl myristate and glycol stearate which enhance drug diffusibility; fatty acid alcohols such as oleyl alcohol and its derivatives; fatty acid amides such as oleamide and its derivatives; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide and dimethylformamide;

salicylic acid; benzyl nicotinate; or higher molecular weight aliphatic surfactants such as lauryl sulfate salts, esters of sorbitol and sorbitol anhydride such as polysorbate. Other suitable enhancers include oleic and linoleic acids, triacetin, ascorbic acid, panthenol, butylated hydroxytoluene, tocopherol, tocopherol acetate, tocopheryl linoleate.

If enhancers are incorporated into the carrier composition, the amount typically ranges up to about 35%, and preferably from about 0.05% to about 20%, by weight based on the dry weight of the total carrier composition.

Use of Dosage Projectile

Typically, the dosage projectile is shot from a launching device such as a gun, pressure or gas activated launcher or the like. Examples of suitable launching devices may be based on similar gas discharge technologies utilized in known dart guns, air guns, crowd control guns and paintball markers currently in production and used in the veterinary, security, law enforcement, hunting, and recreational shooting or paintball industry. In a preferred embodiment a launcher such as described in WO 2012/171064 assigned to SmartVet Pty Ltd is used.

The projectile launcher may include velocity selection means operable to select the velocity at which the projectile is launched. For example the velocity selection means may include pressure-regulating means operable to select the pressure at which the pressurized fluid is released.

The launching propellant may be a pressurized fluid, such as gas or air.

A user triggers the launcher which shoots the projectile at the animal with a velocity sufficient to rupture the projectile upon impact with the animal. This allows the contents of the projectile to contact the skin, coat or fur of the animal, allowing the active agent to be absorbed through the skin of the animal and the impact produces a plurality of shell fragments at least some of which remain associated with the skin, coat or fur of the animal to produce a mark thereby enabling the user to readily discern whether the animal has been treated, where the site of impact was on the animal (if the site of impact is important to the efficacy and absorption of a specific active agent) and whether the projectile has ruptured successfully or not. In particular in embodiments where a marker, such as coloured paint, is used the mark may be easily visualised on animals with a dark coat, skin or fur.

The dosage projectiles may be launched with a single trigger action from a projectile launcher. The projectile launcher may include a selector for selecting the number of projectiles to be launched with a single trigger action. Alternatively, the projectiles may be delivered using a semi-automatic trigger action.

The dosage projectiles, when used to deliver multiple pesticides or doses, may include pesticides which are similar or differing in composition, efficacy, or pharmaceutical action. Accordingly, it is to be understood that the dose administered to an animal may be controlled by selecting the number and type of dosage forms or dosage projectiles to be launched at an animal. In this way, a user can easily adjust the dose required for correctly dosing the animal, by compensating for the size and weight of an animal, and tailor dosing regimens.

It will be appreciated that the treatment may be prophylactic.

EXAMPLES

Example 1

Frangible Shell

| N | Ingredient | Amount (mg) |
|---|---|---|
| 1 | Gelatine Bovine Skin | 536.4 |
| 2 | Glycerol | 63.1-242.5 |
| 3 | Maltitol | 81.2-161.0 |
| 4 | Sorbitol | 80.5-98.2 |
| 5 | Mica | 4.2 |
| 6 | Titanium dioxide | 7.0 |
| 7 | FD&C 6 Sunset yellow | 9.9 |
|   | Total approx. | 800.00 |

Example 2

Projectile Formula
Frangible Shell

| No | Ingredient | % | mg |
|---|---|---|---|
| 1 | Gelatine Bovine Skin | 70 | 560.85 |
| 2 | Sorbitol | 22 | 176.27 |
| 3 | Glycerol | 8 | 64.10 |
|   | Total approx. | 100 | 801.22 |

Fill

| No | Ingredient | Label | Composition w/w % | mg per 10 ml Softgel |
|---|---|---|---|---|
|   | Actives |   |   |   |
| 1 | Piperonyl Butoxide | 700.00 | 7.518 | 700.00 |
| 2 | Lambda Cyhalothrin 97.1% | 140.00 | 1.549 | 144.18 |
|   | Excipients |   |   |   |
| 3 | Corn oil |   | 90.815 | 8,455.82 |
| 4 | Titanium dioxide |   | 0.075 | 7.00 |
| 5 | Lake Yellow Sunset FD&C 6 |   | 0.043 | 4.00 |
|   | Total |   | 100.000 | 9,311.00 |

Example 3

Organoleptic and Physical Characteristics
Test Specifications.
Aspect: Clear round softgel 27.5+/31 1 mm diameter with orange liquid oil product inside.

On testing, the projectiles were found to be able to treat cattle for fly infestation and allow the operator to see which animal in the herd had been treated.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A dosage projectile for remotely administering an active agent to an animal, the dosage projectile configured to contain an active agent and having a frangible shell adapted to fragment on impact with an animal to deliver the active agent to the animal and produce a plurality of shell fragments associated with the animal after impact, wherein the plurality of shell fragments associated with the animal after impact provide a visible mark on the animal; and wherein the frangible shell comprises:
  gelatine in combination with one or more plasticisers; or
  polystyrene or polystyrene derivatives, hydrophilic colloidal materials, polyolefin, polycarbonate, polyamide, polyvinylchloride, resinous compound, thermoplastic polyester, thermoplastic starch polymer blend or a combination thereof.

2. The dosage projectile of claim 1 wherein the plasticiser is glycerol, glycerine, polysorb, maltitol, fructose syrup, glucose syrup, a sugar alcohol or a combination thereof.

3. The dosage projectile according to claim 1 being substantially non-skin piercing.

4. The dosage projectile according to claim 2 wherein the sugar alcohol is selected from the group consisting of glycol, glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol, and polyglycitol.

5. The dosage projectile according to claim 1 wherein the polyolefin is polyprpylene or polyethylene.

6. The dosage projectile according to claim 1 wherein the thermoplastic polyester is polylactic acid.

7. The dosage projectile according to claim 1 wherein the frangible shell includes a marker selected from the group consisting of water insoluble dye, water soluble dye, pigment, Lake dye, infra-red dye, ultraviolet dye, a luminescent dye, coloured paint, reflective material, refractive material, fluorescent material, and luminescent material.

8. The dosage projectile according to claim 1 wherein the shell fragments mark the animal for a period of time to allow confirmation that an animal has been treated.

9. The dosage projectile according to claim 8 wherein the animal is marked for up to about 72 hours.

10. The dosage projectile according to claim 1 configured to be remotely delivered over a distance.

11. The dosage projectile according to claim 1 wherein the active agent is selected from the group consisting of pharmaceutical, veterinary pharmaceutical, vaccine or immunogenic compound, parasiticide, pesticide, contraceptive, and health supplement.

12. The dosage projectile according to claim 11 wherein the pharmaceutical or veterinary pharmaceutical is selected from the group consisting of macrocyclic lactones, synthetic pyrethroids, insect growth regulators, anthelminitics, steroid hormones, anaesthetic agents and analgesics, antibacterial or antibiotic agents, anthelmintic, anti-trematodal, anticestodal, anti-parasitic/parasiticidal agents, acaricidal agents, anti-fungal agents, antihistamine agents, antiviral agents, anxiolytic agents, β-adrenergic agonists, bronchodilators, anti-allergy agents, cardioactive agents, central nervous system stimulants and agents, cholinergic agents, anti-cholinergic agents, anti-emetic agents, and muscle relaxants.

13. The dosage projectile according to claim 11 wherein the health supplement is selected from the group consisting of vitamin and mineral.

14. A method of remotely treating an animal comprising:
  launching a projectile according to claim 1 at the animal;
  impacting the projectile on the animal causing the frangible shell of the projectile to shatter and release the active agent to the animal, and
  producing a plurality of shell fragments associated with the animal after impact to provide a visible mark on the animal.

15. The method of claim 14 wherein there is no substantial piercing of the skin of the animal by the projectile.

* * * * *